United States Patent [19]

Rovati et al.

[11] Patent Number: 5,177,099
[45] Date of Patent: Jan. 5, 1993

[54] DICHLORO-SUBSTITUTED IMIDAZOLE DERIVATIVES AS ANTIFUNGAL AGENTS

[75] Inventors: Romeo A. Rovati; Ricardo C. Mestres, both of Barcelona, Spain

[73] Assignee: Sociedad Espanola de Especialidades Farmaco-Terapeuticas S.A., Barcelona, Spain

[21] Appl. No.: 887,103

[22] Filed: May 19, 1992

Related U.S. Application Data

[63] Continuation of Ser. No. 506,870, Apr. 9, 1990, abandoned.

[30] Foreign Application Priority Data

Apr. 10, 1989 [ES] Spain ................................ 8901237

[51] Int. Cl.$^5$ ................ A61K 31/415; C07D 233/58
[52] U.S. Cl. ................................ 514/399; 548/345.1
[58] Field of Search ................ 548/341; 514/399

[56] References Cited

U.S. PATENT DOCUMENTS

| | | | |
|---|---|---|---|
| 3,660,577 | 5/1972 | Buchel et al. | 548/335 |
| 3,666,862 | 5/1972 | Buchel et al. | 424/273 |
| 3,764,609 | 10/1973 | Van Der Stelt | 548/335 |
| 4,420,474 | 12/1983 | Sykes | 424/121 |

FOREIGN PATENT DOCUMENTS 1593417  7/1981  United Kingdom .

OTHER PUBLICATIONS

PCT Publication No. WO88/03138 of Schering Corporation May 1988.

Primary Examiner—Patricia L. Morris
Attorney, Agent, or Firm—Trask, Britt & Rossa

[57] ABSTRACT

Dichloro-substituted 1-(5H-dibenzo[a,d]cyclohepten-5-yl)-1H-imidazole compounds of formula (I), in which —X— is either —CH$_2$—CH$_2$— or —CH=CH—, and their pharmaceutically acceptable addition salts, preferably the nitric acid ones. Products of formula (I) are prepared from products of formula (VI) where Z represents a leaving group such as halogen, by treatment with an excess of imidazole in dimethylformamide. Products (I) show an antifungal activity comparable -or superior- to antimycotics in the market, such as Clotrimazole and Bifonazole.

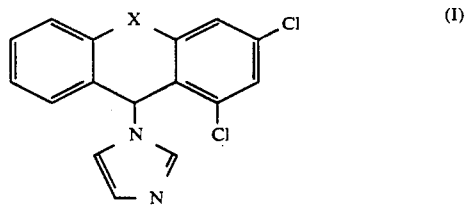

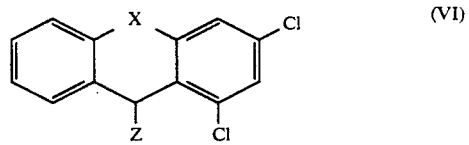

9 Claims, No Drawings

DICHLORO-SUBSTITUTED IMIDAZOLE DERIVATIVES AS ANTIFUNGAL AGENTS

This application is a continuation of application Ser. No. 07/506,870, filed Apr. 9, 1990, now abandoned.

This invention refers to the two new dichlorosubstituted 1-(5H-dibenzo[a,d]cyclohepten-5-yl)-1H-imidazole compounds of formula (I), in which —X— is either —$CH_2$—$CH_2$— or —CH=CH—, and their pharmaceutically acceptable addition salts, a process for their production, and their use in the preparation of anti-fungal pharmaceutical and veterinary compositions.

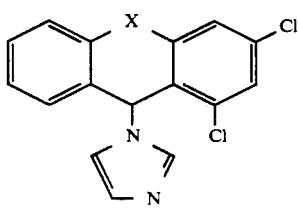

(I)

BACKGROUND ART

It is known that N-tritylimidazole derivatives show fungicide activities. For instance, U.S. Pat. No. 3,660,577 discloses antimycotics of the general formula (II), wherein R, $R_1$ and $R_2$ denote hydrogen, lower alkyl radicals and phenyl; X stands for alkyl groups or for electronegative substituents; and n denotes an integer from 0 to 2, and n may have different meanings in the individual benzene rings.

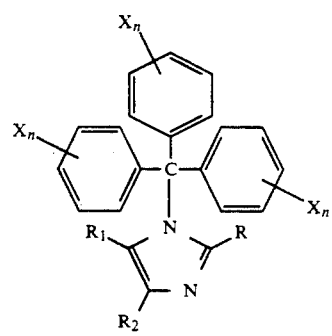

(II)

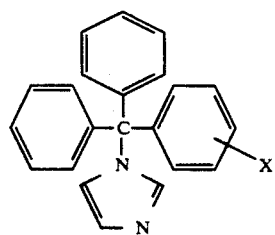

(III)

It is known that, in general, among the very many prducts embraced by general formula (II), mono-substituted ones are more active as antifungal agents than poly-substituted ones. Thus, for instance, FR 1.600.990 discloses antimycotics of general formula (III), where X stands for several substituents, halogens included. This document describes comparative tests of monosubstituted halogen derivatives versus analogous di- and tri-substituted ones; from the results it is clear that mono-substituted derivatives have higher antifungal activities. In fact, the most successful commercial product included in general formula (III) is the monosubstituted chloro derivative named Clotrimazole.

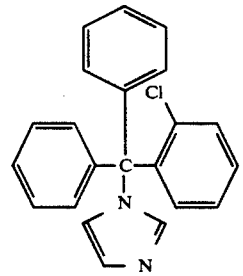

(Clotrimazole)

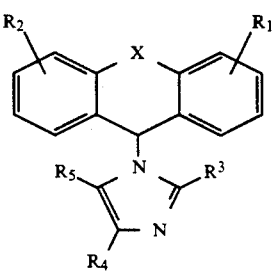

(IV)

U.S. Pat. No. 3,764,609 disclosed 1-(5H-dibenzo[a,d]cyclohepten-5-yl)-1H-imidazole derivatives of general formula (IV), wherein $R_1$ and $R_2$ are the same or different and each represents a hydrogen or halogen atom or a lower alkyl group, $R_3$, $R_4$ and $R_5$ represent a hydrogen atom or an alkyl group, X represents a single bond, a —$CH_2$—$CH_2$—, —$CH_2$—$CH_2$—$CH_2$— or —CH=CH— group or a group —$CH_2$—CHHal— wherein Hal represents a chlorine or bromine atom. It is said that products of general formula (IV) possess fungicidal activity, although no data is given in this document. It is noteworthy that *general formula (IV) does not embrace any product di-substituted in the same phenyl ring.* Actually no di-substituted product is described in this document, even with substitution in different rings. Among the described products in this patent, the one which is structurally closest to those of the present invention is the product of formula (V), which has a bromine atom in position 3.

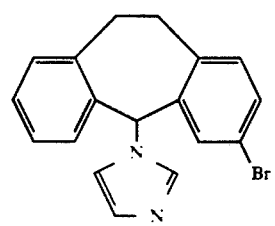

(V)

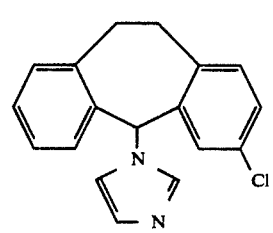

(SQ 80896)

Squibb U.S. Pat. No. 4,420,474 discloses synergistic antifungal compositions of antimycotics and Azalomycin F. In its Table I 1-(3-chloro-10,11-dihydro-5H-dibenzo[a,d]dicyclohepten-5-yl)-1H-imidazole is mentioned with the company name SQ 80896, but without giving any indication for its preparation or use. To the best of our knowledge, SQ 80896 is structurally the closest product to the products of the present invention, ever described. In any case, the pharmacological data in Table I of U.S. Pat. No. 4,420,474 clearly show that *SQ 80896 is considerably less active than Clotrimazole* (according to MIC parameters against *Candida alibicans*).

Despite the usefulness of the already known commercial antifungal agents, research in this field is very intensive because some fungi species have become resistant to old compounds (particularly to the widespread Clotrimazole). This represents a serious problem, specially in hospitals and big towns. It is very important to search for new antifungals with powerful action and wide spectrum; but it is also important to provide new antifungals active against a limited number of fungal infections, some of which could be resistant to old products. Thus, new compounds (Econazole, Miconazole, ... and notably Bifonazole) are being introduced in the market as soon as they show any antifungal activity against some species similar to, or higher than, the activity of old products, notably of Clotrimazole which is still the most active commercial product against some species.

DISCLOSURE OF THE INVENTION

The above-mentioned state of the art clearly shows that there was a general trend pointing away from the screening of poly-halogen substituted compounds, in the search for new imidazole derivatives with antifungal activity. This tendency was very clear for N-tritylimidazole type of general formula (II), as illustrated by the teaching of the above-mentioned patent FR 1.600.990.

We have observed a similar trend in the course of our own research. Thus, for instance, we have prepared product WAS 2162 (as a nitric acid salt) and we have found that it is considerably less active than Clotrimazole, as illustrated by the results of the Table of Example 3.

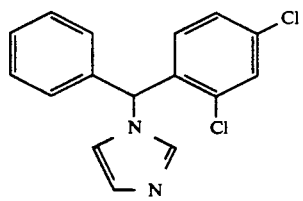

(WAS 2162)

Substitution of imidazole derivatives of the(dibenzo[a,d]cyclohepten-5-yl)-1H-imidazole type (general formula IV) for the classical N-tritylimidazole derivatives (general formula III) did not appear a promising trend in the field of antimycotics. Actually, to our knowledge, no derivative of those included in general formula (IV) has ever been marketed. As mentioned above, U.S. Pat. No. 4,420,474 patent mentions that SQ 80896 is considerably less active than Clotrimazole. We have also prepared and tested SQ 80896 and, according to our experience (cfr. e.g. the table of Example 3), this product is considerably less active than Clotrimazole.

Despite the two trends mentioned above, we have unexpectedly found that dichloro-substituted 1-(5H-dibenzo[a,d]cyclohepten-5-yl)-1H-imidazole compounds of formula (I), where —X— is either a —CH$_2$—CH$_2$— or a —CH=CH— group, and their pharmaceutically acceptable salts, surprisingly have a antifungal activity comparable —or superior— to that of some antifungals on the market, in particular Clotrimazole and Bifonazole. This is clearly illustrated in the pharmacological comparative test of Examples 3-7. Thus, according to one main aspect of the invention, new products of formula (I) are provided to fight against fungal infection. As products (I) belong to a chemical class never marketed before, it is almost sure that many fungi species have not developed resistance to them, what constitutes an advantage over other already-used products.

The number and position of chloro substitution, together with the lack of mobility provided to the molecule by the —CH$_2$—CH$_2$— or the —CH=CH— bridges, are two simultaneous structural features which are essential for the antifungal activity. Thus, if the chloro substitution is different (as is product SQ 80896), or if the bridge disappears (as in product WAS 2162), the antifungal activity dramatically diminishes.

General formula (I) embraces two main embodiments of the invention, namely, compound 1-(2,4-dichloro-10,11-dihydro-5H-dibenzo[a,d]cyclohepten-5-yl)-1H-imidazole and its pharmaceutical acceptable salts, and compound 1-(2,4-dichloro-5H-dibenzo[a,d]cyclohepten-5-yl)-1H-imidazole and its pharmaceutical acceptable salts. Their nitric acid salts, prepared and described here for the first time, are respectively denoted WAS 2160 and WAS 2169 in the following. The names and formulas used here represent racemic mixtures. Although it is expected than one enantiomer will have more activity than its mirror-image one, all stereoisomers and their mixtures are to be considered subject-matter of the present invention.

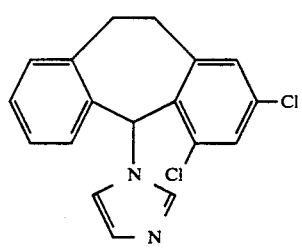

(WAS 2160)

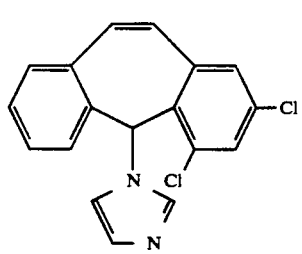

(WAS 2169)

Another main aspect of the invention are pharmaceutical compositions for treating fungal infections in humans and animals which comprises an antifungal effective amount of a compound of formula (I) or a pharmaceutically acceptable salt thereof, in combination with a pharmaceutically acceptable excipient or carrier. A preliminary test in rabbits (cfr. Example 8) clearly shows that products of the invention are innocuous and totally tolerated by the eye, the skin and the vagina.

The invention also provides the use of a compound of formula (I) or a pharmaceutically acceptable salt thereof in the preparation of a medicament for treating fungal infections in humans or animals.

Pharmaceutically acceptable salts of the products of the present invention are those obtained from physiologically tolerated inorganic acids, such as nitric, phosphoric, sulphuric or hydrochloric, sulphonic acids, and carboxylic or hidroxycarboxylic acids, such as acetic, tartaric, salicylic, citric, ascorbic, etc. In a preferred embodiment, the salt is the one obtained from nitric acid.

By pharmaceutically acceptable excipients or carriers there are to be understood solid, semi-solid or liquid diluents, fillers and formulation auxiliaries of all kinds. Tablet, pills, capsules, granules, solutions, suspensions, emulsions, suppositories, pastes, ointments, gels, creams, lotions, powders and sprays containing products of formula (I) may be mentioned as possible pharmaceutical compositions.

Another main aspect of the invention is a process for preparing a compound of formula (I) or a pharmaceutically acceptable salt thereof, which comprises reacting a compound of formula (VI), where Z is a halogen group or a sulphonate group (e.g. methanesulphonate, benzenesulphonate or tosylate), with imidazole or an equivalent nucleophilic reactant (e.g. an imidazole salt or trimethylsilylimidazole), in a polar inert solvent (e.g. dimethylformamide), in the presence of a base (e.g. an excess of imidazole, triethylamine, potassium carbonate or equivalent) to neutralise the acid formed; and, if a salt is desired, the subsequent addition of the corresponding acid.

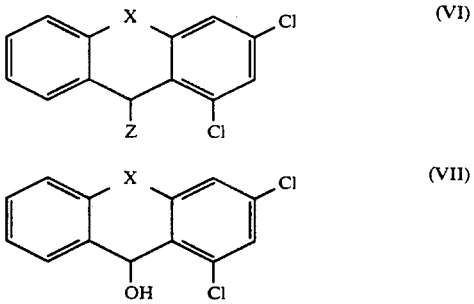

Preferred embodiments of the invention are the following: Z is Cl in intermediate (VI), this being obtained from (VII) with thionyl chloride; the reaction is carried out in excess of imidazole, without addition of another base, and in dimethylformamide as solvent; alcohols (VII) are obtained from ketones (VIII) by standard reduction methods such a catalytic hydrogenation or treatment with hydrides, preferably with sodium borohydride.

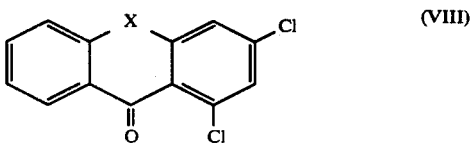

The nucleophilic substitution reactions of the process of the present invention have the particular difficulty of the presence of an steric hindrance due to the great proximity of the chloro substituent nearest to the reaction center. However, under the preferred conditions of this invention (excess of imidazole, in dimethylformamide under reflux, for 6 h, with subsequent addition of nitric acid), yields are high.

Products of formula (VI) can be prepared by treatment of alcohols of formula (VII) with standard reagents of Organic Chemistry. Thus, e.g., when Z is Cl, thionyl chloride can be used; when Z is Br, phosphorous tribromide in pyridine can be used; when Z is tosylate, tosyl chloride can be used; etc.

Alcohols of formula (VII) can be prepared by reduction of the corresponding ketones by standard organic synthetic methods, such as treatment with sodium borohydride or by catalytic hydrogenation. The two ketones (VIII) required for the preparation of the products of the present invention have been described in the literature (cfr. X. Cirera, PhD Dissertation, Instituto Quimico de Sarriá, Barcelona, 1983). Final products (I) and intermediates (VII, and VI with Z=Cl) have not been described before.

The present invention is illustrated by the following non-limitative examples.

EXAMPLE 1

1-(2,4-Dichloro-10,11-dihydro-5H-dibenzo[a,d[cyclohepten-5-yl)-1H-imidazole nitrate (WAS 2160)

a) A solution of 50 mmol of 2,4-dichloro-10,11-dihydro-5H-dibenzo[a,d]cyclohepten-5-one in 100 mL of methanol was placed in a 250-mL flask provided with magnetic stirring, reflux condenser and addition funnel. Then, a solution of 50 mmol of sodium borohydride in 5 mL of water and 15 mL of methanol was added during 15 min. The mixture was shaken at room temperature for three hours and it was brought to pH=1 with concentrated hydrochloric acid. The solvent was removed under vacuum. The residue was dissolved in 75 mL of chloroform and washed with 2×50 mL of water. The organic phase was dried with anhydrous magnesium sulphate and filtered. The solvent was removed under vacuum. The residue was used without more purification in the next step. I.R. (KBr): 3500–3200, 3020, 2940, 1590, 990 cm$^{-1}$. The disappearance of the carbonyl band was observed.

b) The crude material from the previous step was dissolved in 100 mL of methylene chloride. To this solution 75 mmol of thionyl chloride were added at room temperature for five minutes. The solvent was removed under vacuum and the residue was dissolved in 50 mL of thionyl chloride and heated under reflux for an hour. The excess thionyl chloride was distilled under vacuum; 50 mL of toluene were added; the solvent was removed under vacuum and the residue was used without more purification in the next step. I.R. (KBr): 3030–3010, 2940, 1585 cm$^{-1}$. The disappearance of the bands corresponding to hydroxyl stretching was observed.

c) The crude material from the previous step was dissolved in 100 mL of dimethylformamide. Then 200 mmol of imidazole were added and the mixture was heated under reflux for six hours. The solvent was removed under vacuum; the residue was dissolved in 75 mL of chloroform and washed with 3×50 mL of water. The organic phase was dried with anhydrous magnesium sulphate and filtered. The solvent was removed under vacuum. The residue was dissolved in 50 mL of isopropyl ether and 25 mL of isopropyl alcohol. Then 60% (density=1.38) nitric acid was added until total precipitation of the title compound was reached. After filtration, the solid was recrystallised from isopropyl ether/isopropyl alcohol. Overall yield: 56%. M.p. 173°-174° C. I.R. (KBr): 3160, 3100, 3000-2400 (N—H), 1590, 1400, 1320, 1290, 895, 860 cm$^{-1}$; $^1$H—RMN (DCCl$_3$/CD$_3$OD): $\delta$=8.2/s (1H), 7.5-6.7/sc (9H), 2.9-2.6/sc(4H).

EXAMPLE 2

1-(2,4-dichloro-5H-dibenzo[a,d]cyclohepten-5-yl)-1H-imidazole nitrate (WAS 2169)

a) A solution of 50 mmol of 2,4-dichloro-5H-dibenzo[a,d]cyclohepten-5-one in 100 mL of methanol was placed in a 250-mL flask provided with magnetic stirring, reflux condenser and addition funnel. A solution of 50 mmol of sodium borohydride in 5 mL of water and 15 mL of methanol was added for 15 min. The mixture was shaken at room temperature for three hours and brought to pH=1 with concentrated hydrochloric acid. The solvent was removed under vacuum. The residue was dissolved in 75 mL of chloroform and washed with 2×50 mL of water. The organic phase was dried with anhydrous magnesium sulphate and filtered. The solvent was removed under vacuum, and the residue was used without more purification in the next step. I.R. (KBr): 3500-3200, 3020, 1595, 1000 cm$^{-1}$. The disappearance of the carbonyl band was observed.

b) The crude material from the previous step was dissolved in 100 mL of methylene chloride. Then 75 mmol of thionyl chloride were added at room temperature for five minutes. The solvent was removed under vacuum and the residue was dissolved in 50 mL of thionyl chloride. The mixture was heated under reflux for an hour. The excess of thionyl chloride was distilled under vacuum; 50 mL of toluene were added; the solvent was removed under vacuum and the residue was used without more purification in the next step. I.R. (KBr): 3030-3000, 2940, 1580 cm$^{-1}$. The disappearance of the bands corresponding to the stretching of the hydroxyl group was observed.

c) The crude material from the previous step was dissolved in 100 mL of dimethylformamide. Then 200 mmol of imidazole were added and the mixture was heated under reflux for six hours. The solvent was removed under vacuum. The residue was dissolved in 75 mL of chloroform and washed with 3×50 mL of water. The organic phase was dried with anhydrous magnesium sulphate and filtered. The solvent was removed under vacuum. The residue was collected in 50 mL of isopropyl ether and 25 mL of isopropyl alcohol. Then 60% (density=1.38) nitric acid was added until total precipitation of the title compound was reached. After filtration, the solid was recrystallised from isopropyl ether/isopropyl alcohol. Overall yield: 48%. M.p.: 165°-167° C. I.R. (KBr): 3160, 3000-2300 (N—H), 1580, 1500, 1320, 1295, 890, 850, 750 cm$^{-1}$ $^1$H-RMN (DCCl$_3$/CD$_3$OD): $\delta$=7.75/s(1H), 7.6-7.1sc(9H), 6.8/d(1H), 6.5/m(1H).

EXAMPLE 3

In vitro activity against Candida tropicalis CECT 1440.

This pharmacological test allows a comparison of the activities of the two products of the present invention (WAS 2160 and WAS 2169) with the activities of the structurally closest described product (SQ 0896), the structurally closest commercial product (Clotrimazole) and the analogue product without the seven-membered ring (WAS 2162). MIC (Minimum Inhibitory Concentration, in fg/mL) and RIF (Relative Inhibition Factor) parameters were determined in a standard way, obtaining the results of the table (WAS 2162 is the nitric acid salt of 1-[(2,4-dichlorophenyl)phenylmethyl]-1H-imidazole, prepared at our laboratory).

| Product | Candida tropicalis | |
|---|---|---|
| | MIC | RIF |
| WAS 2160 | 7.79 | 39.31 |
| WAS 2169 | 16.13 | 54.94 |
| SQ 80896 | >100 | 83.96 |
| WAS 2162 | >100 | 94.47 |
| Clotrimazole | 11.81 | 43.05 |

EXAMPLE 4

In Vitro Activity Against 116 Strains of Yeasts and 45 Strains of Dermatophytes

MIC-s were determined by the method of progressive double dilutions in a liquid medium, using sterile microplates. The culture medium used was the Sabouraud broth with gentamycin (100 mg/1000 mL). The results obtained in comparative tests with WAS 2169, WAS 2160 and Clotrimazole (Clot.) are shown in the following table.

| | Yeasts and Dermatophytes | | | |
|---|---|---|---|---|
| | WAS 2160 | WAS 2169 | CLOT. | BIF. |
| C. albicans | 2,25 | 1,98 | 2,43 | 12,10 |
| C. tropicalis | 3,44 | 7,58 | 3,51 | 72,67 |
| C. parapsilosis | 2,06 | 1,08 | 2,36 | 58,97 |
| C. Krusei | 3,17 | 5,61 | 6,18 | 50,50 |
| Torulopsis glabrata | 1,25 | 6,33 | 6,29 | 14,88 |
| Microsporum canis | 0,39 | 0,06 | 2,69 | 3,12 |
| Trichoph. mentagrophytes | 0,17 | 0,17 | 0,23 | 1,48 |
| Trich. rubrum | 0,54 | 0,30 | 0,31 | 1,19 |
| M. gypseum | 1,05 | 0,08 | 0,97 | 6,25 |
| Epidermophyton floccosum | 0,32 | — | 0,09 | 0,02 |
| T. tonsurans | 0,19 | — | 0,90 | 1,20 |

EXAMPLE 5

In Vivo Test of Protection Against Experimentally-induced Dermatophytosis n the Guinea Pig, Caused by *Trichophyton mentagrophytes*

Two double-blind comparative tests were carried out, with the following results:

| | In vivo protection against dermatophytosis | |
|---|---|---|
| Product | % of negative cultures after treatment | |
| WAS 2160 | 50% | |
| Bifonazole | 39% | (test I) |
| WAS 2169 | 81,8% | |
| Bifonazole | 0% | (test II) |

EXAMPLE 6

In Vivo Test of Antifungal Activity Against Candidiosis in Guinea Pig

A double-blind comparative test was carried out with WAS 2160 and Clotrimazole, with the following results:

| | In vivo protection against candidiosis | |
|---|---|---|
| Product tested | % of negative cultures after treatment | % of animals with total clin. healing |
| WAS 2160 | 100% | 60% |
| Clotrimazole | 100% | 30% |

EXAMPLE 7

In Vitro Test Against 30 Strains of *Malassezia Furfur* (Pytiosporum)

A double-blind comparative test was carried out with WAS 2160, Clotrimazole and Bifonazole, with the results of the table. (PIC=Partial Inhibitory Concentration: growth inhibition greater than 50% in relation to controls).

| | In vitro protection against *Malassezia fufur* | |
|---|---|---|
| Product tested | % of strains with MIC lower than 40 μg/mL | % of strains with PIC lower than 40 μg/mL |
| WAS 2160 | 40% | 60% |
| Clotrimazole | 33% | 56% |
| Bifonazole | 83% | 50% |

EXAMPLE 8

Tolerance Test of WAS 2160 in Rabbits

Product WAS 2160 proved to be innocuous and totally tolerated by the eye, the skin and the vagina.

What is claimed is:

1. Dichloro-substituted 1-(5H-dibenzo[a,d]cyclohepten-5-yl)-1H-imidazole compound of formula (I), where —X— is either a —CH$_2$—CH$_2$— or a —CH=CH— group, and pharmaceutically acceptable salts thereof.

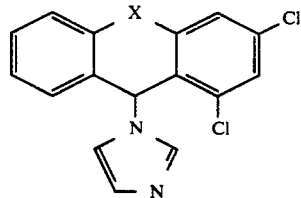

(I)

2. A pharmaceutical composition for treating fungal infections in humans and animals which comprises an antifungal effective amount of a compound of formula (I) in claim 1 or a pharmaceutically acceptable salt thereof, in combination with a pharmaceutically acceptable excipient or carrier.

3. Method for treating antifungal infections in humans and animals which comprises administering an antifungal effective amount of a compound of formula (I) in claim 1 or a pharmaceutically acceptable salt thereof, in combination with a pharmaceutically acceptable excipient or carrier.

4. The compound according to claim 1 wherein —X— is —CH$_2$—CH$_2$—, such compound being 1-(2,4-dichloro-10,11-dihydro-5H-dibenzo[a,d]cyclohepten-5-yl)-1H-imidazole, or a pharmaceutical acceptable salt thereof.

5. A pharmaceutical composition for treating fungal infections in humans and animals according to claim 2 which comprises an antifungal effective amount of 1-(2,4-dichloro-10,11-dihydro-5H-dibenzo[a,d]cyclohepten-5-yl)-1H-imidazole or a pharmaceutical acceptable salt thereof in combination with a pharmaceutically acceptable excipient or carrier.

6. Method according to claim 1 which comprises administering an antifungal effective amount of 1-(2,4-dichloro-10,11-dihydro-5H-dibenzo[a,d]cyclohepten-5-yl) -1H-imidazole or a pharmaceutical acceptable salt thereof, in combination with a pharmaceutically acceptable excipient or carrier.

7. The compound according to claim 1 wherein —X— is —CH=CH—, such compound being 1-(2,4-dichloro-5H-dibenzo[a,d]cyclohepten-5-yl)-1H-imidazole, or a pharmaceutical acceptable salt thereof.

8. A pharmaceutical composition for treating fungal infections in humans and animals according to claim 2 which comprises an antifungal effective amount of 1-(2,4-dichloro-5H-dibenzo[a,d]cyclohepten-5-yl)-1H-imidazole or a pharmaceutical acceptable salt thereof in combination with a pharmaceutically acceptable excipient or carrier.

9. Method for treating antifungal infections in humans and animals which comprises administering an antifungal effective amount of 1-(2,4-dichloro-5H-dibenzo[a,d]cyclohepten-5-yl)-1H-imidazole or a pharmaceutical acceptable salt thereof, in combination with a pharmaceutically acceptable excipient or carrier.

* * * * *

UNITED STATES PATENT AND TRADEMARK OFFICE
CERTIFICATE OF CORRECTION

PATENT NO. : 5,177,099
DATED : 1/5/93
INVENTOR(S) : Romeo Andreoli Rovati, Ricardo Cepero Mestres It is certified that error appears in the above-indentified patent and that said Letters Patent is hereby corrected as shown below:

On the title page, under item [19], "Rovati et al." should read --Andreoli Rovati, et al.--;

On the title page, item [54], the inventors names should be corrected to read --Romeo Andreoli Rovati-- and --Ricardo Cepero Mestres--;

In Column 1, line 60, change "prducts" to --products--;

In Column 7, line 58, insert a period after "cm⁻¹";

In Column 7, line 68, change "0896" to --80896--;

In Column 8, line 55, change "n" to --in--;

Signed and Sealed this

Fifteenth Day of February, 1994

Attest:

BRUCE LEHMAN

Attesting Officer     Commissioner of Patents and Trademarks